United States Patent [19]

Edwards et al.

[11] Patent Number: 5,360,529
[45] Date of Patent: Nov. 1, 1994

[54] REFERENCE HALF-CELL ELECTRODE

[75] Inventors: Stephen J. Edwards, Pinner; John Chapples, Harrow; Kevin J. Parr, Harrow Weald, all of England; Philippe G. Robert, Givry, France

[73] Assignee: Eastman Kodak Company, Rochester, N.Y.

[21] Appl. No.: 39,351

[22] PCT Filed: Aug. 19, 1992

[86] PCT No.: PCT/EP92/01884
§ 371 Date: Apr. 21, 1993
§ 102(e) Date: Apr. 21, 1993

[87] PCT Pub. No.: WO93/04360
PCT Pub. Date: Mar. 4, 1993

[30] Foreign Application Priority Data

Aug. 24, 1991 [GB] United Kingdom ............ 9118300

[51] Int. Cl.$^5$ ............................................. G01N 27/26
[52] U.S. Cl. ............................ 204/435; 204/416; 204/433
[58] Field of Search ............... 204/433, 435, 153.13, 204/416, 418, 419

[56] References Cited

U.S. PATENT DOCUMENTS 3,912,614 10/1975 Spracklen et al. ............ 204/403
4,959,138 9/1990 Brinkmann et al. ............ 204/435

FOREIGN PATENT DOCUMENTS 0313657 5/1989 European Pat. Off. .
0155727 9/1990 European Pat. Off. .
0393188 10/1990 European Pat. Off. .
3405431 3/1985 Germany .
900248 7/1962 United Kingdom .

Primary Examiner—John Niebling
Assistant Examiner—Bruce F. Bell
Attorney, Agent, or Firm—Paul A. Leipold

[57] ABSTRACT

A half-cell reference electrode comprises an electrode member in electrochemical contact with at least one gelled electrolyte solution which itself is contactable with the liquid to be tested wherein the gelling agent comprises a polymer containing acrylamide units substituted with a group or groups which lower the polymer's tendency to hydrolyse compared to polyacrylamide while providing a polymer that can form a gelled solution in 2.6M sodium/potassium nitrate solution (2.21M potassium nitrate and 0.39M sodium nitrate) comprising at least 75% (w/w) sodium/potassium nitrate solution.

29 Claims, 5 Drawing Sheets

REFERENCE HALF-CELL ELECTRODE

This invention relates to reference half-cell electrodes and in particular to electrodes intended for use in the measurement of halide ions.

In electroanalytical measurements, a reference electrode is used in conjunction with a sensing electrode. When both electrodes are immersed in a solution of an ionic salt, a potential difference is established between the electrodes, whose magnitude is a function of the concentration of the dissolved ionic species.

Examples of commercial reference electrodes, which are commonly used for such purposes include saturated aqueous calomel and silver/silver chloride electrodes. These comprise an internal reference element which is immersed in a highly concentrated salt solution. This serves the purpose of maintaining a constant ionic strength environment for the reference element.

Many electrodes suffer from inherent disadvantages that result from leakage of the electrolyte solution. Firstly, the electrode solutions require periodic replenishment which results in regular maintainance being necessary. This can be inconvenient, costly and time consuming, especially in an industrial environment. Secondly, leakage may cause the electrode to be unsuitable for particular industrial or medical applications where contamination poses a problem.

Attempts to overcome these problems have focussed on the replacement of the electrolyte solution with a gelled electrolyte equivalent. These types of reference electrode have a much lower rate of seepage of electrolyte from within the gel and consequently only require minimal maintenance until the electrolyte is exhausted.

British Patent Specification 1 353 209 describes a single junction electrode comprising a silver wire coated with silver chloride surrounded by a polyolefin tube filled with a gel containing potassium chloride. In use the open end of the polyolefin tube filled with the gel is placed in the solution to be measured. However it is stated that the electrode will need renewal and this is done by cutting the lower end of the polyolefin tube thus exposing a fresh surface of the gel. Example 3 indicates that such renewal needs to be carried out about every 24 hours. Such variable behaviour we call long term variability.

A commonly used polymer gelling agent is polyacrylamide.

If it is desired to make sure that absolutely none of the electrolyte in the electrode contaminates the liquid being tested it is known to add a further electrolyte bridge comprising a different salt (which is tolerated by the test liquid). Such a double junction electrode is described in German Specification 3415089 A1. Unlike the electrode described in the British specification however the gelled electrolyte is not in direct contact with the liquid being tested because there is an additional ion exchanger unit therebetween.

Reference electrodes, in addition to displaying long term variability due to junction contamination also show short term variability possibly caused by changes of the silver wire half-cell potential or temperature effects. Variability can also occur when the reference electrode is immersed in solutions of varying ionic strength, such as environmental samples. This is caused by junction potentials developing at the electrolyte/sample interface. Electrodes subject to both long and short term variations require frequent calibration and this is clearly undesirable.

According to the present invention there is provided a half-cell reference electrode comprising an electrode member in electrochemical contact with at least one gelled electrolyte solution which itself is contactable with the liquid to be tested wherein the gelling agent comprises a polymer containing acrylamide units substituted with a group or groups which lower the polymer's tendency to hydrolyse compared to polyacrylamide while providing a polymer that can form a gelled solution in 2.6M sodium/potassium nitrate solution (2.21M potassium nitrate and 0.39M sodium nitrate) comprising at least 75% (w/w) sodium/potassium nitrate solution.

It is preferred that the polymer can form a gelled solution in the 2.6M sodium/potassium nitrate solution comprising from 75% to 90%, especially from 80% to 90%, (w/w) sodium/potassium nitrate solution.

Preferably, the electrolyte is present in the gel in solution and not in suspension.

An electrode according to the invention may have a first gelled electrolyte solution itself in contact with a second gelled electrolyte solution which is contactable with the liquid to be tested. Alternatively the first gelled electrolyte can be replaced by a viscous electrolyte solution which is in contact with the second gelled electrolyte solution. Such an electrode is referred to herein as a double junction electrode.

When the electrode member is in contact with a viscous electrolyte solution rather than a gelled electrolyte, this ensures that the electrode member maintains good electrochemical contact with the first electrolyte.

In another form the electrode of the present invention may have a third gelled electrolyte solution in contact with the second gelled electrolyte solution, said third gelled electrolyte being contactable with the liquid to be tested. Such an electrode is referred to herein as a triple junction electrode.

The present half-cell reference electrodes display both long and short term stability. In particular the gel/sample interface is stable over long periods and they are stable to short term variations of ion concentration or temperature of the sample.

The polymer preferably comprises units derived from tris(hydroxymethyl)methyl acrylamide. These units may be cross-linked, e.g. with N,N'-methylene-bis-acrylamide, tetraethylene glycol dimethacrylate, 1,4-butanediol dimethacrylate, ethylene diarylate or ethylene glycol dimethacrylate.

The electrode may comprise a reference element of the calomel or redox half-cell type, e.g. iodine/iodide, or it may have a silver/silver chloride electrode member, either of the silver wire or cartridge type, in contact with a gelled or viscous potassium chloride/silver chloride solution.

Preferably, the second gelled electrolyte comprises a potassium chloride solution.

In another preferred embodiment, the second or third gelled electrolyte comprises a potassium nitrate or a mixed potassium and sodium nitrate solution.

It is sometimes advantageous to add to the electrolyte solution one or more of glycerol, ethylene glycol, polyethylene glycol, polyvinyl alcohol, silica gel or a polyoxyethylene-polyoxypropylene-polyoxyethylene triblock copolymer as a water evaporation inhibitor to make the electrode less sensitive to dry storage, to improve the adhesion to the external wall or to improve the mechanical properties of the gel.

The electrode may be housed in a flexible or semi-flexible tube optionally connected to a more rigid upper body. Alternatively the whole may be contained in a glass outer case.

In use, a half-cell reference electrode according to the invention and a sensing electrode for the ions to be measured are each contacted with the liquid to be tested and the potential difference established between the electrodes is measured.

The electrode of the invention may be contacted directly with the liquid e.g. by partial immersion or contact may be made indirectly through a salt bridge. Use of a salt bridge enables the life of the electrode to be prolonged and enables the electrode to be maintained at constant temperature when the temperature of the test liquid is varied.

The salt bridge may comprise an aqueous solution of an equitransferant electrolyte e.g. potassium chloride or mixed potassium/sodium nitrates. Preferably, the electrolyte solution is gelled.

The junction of the salt bridge which contacts the liquid under test may be a ceramic plug, wick, glass sleeve or any other commonly used form of junction. Alternatively, the junction of the salt bridge may be a gelled electrolyte.

BRIEF DESCRIPTION OF THE DRAWINGS

FIG. 1 is a double junction electrode comprising a polyethylene or glass tube (1) with a closure (2) through which is mounted the electrode member (3) comprising a silver wire and silver chloride coating (4) and an electrical connection to the outside (not shown). The electrode member is surrounded by a viscous KCl/AgCl solution (5) and below and in contact therewith is a gelled KCl solution. The aperture (7) allows electrochemical contact between (5) and the solution to be tested.

FIG. 2 is a triple junction electrode comprising the same components as in FIG. 2 and, in addition, another section of gelled electrolyte comprising $KNO_3$/$NaNO_3$.

FIG. 3 is another electrode comprising two glass vessels (10 and 11), the inner vessel containing the silver/silver chloride electrode member (3,4), the viscous KCl/AgCl solution (5) and the gelled KCl solution (6) while the outer vessel contains the mixed $KNO_3$/$NaNO_3$ gelled solution. An additional aperture (9) is provided to allow electrochemical contact between the electrolytes (6) and (8).

FIG. 7 is a double junction electrode comprising two glass vessels (10 and 11), the inner coiled vessel (11) containing the silver/silver chloride electrode member (3,4) and the viscous or gelled KCl/AgCl solution (5) (not shown) while the outer vessel (10) contains the gelled KCl solution (6) (not shown). The aperture (9) at the open end of the coiled vessel (11) provides electrochemical contact between the electrolytes (5) and (6).

The following Examples are included for a better understanding of the invention.

EXAMPLE 1

Figure 1:
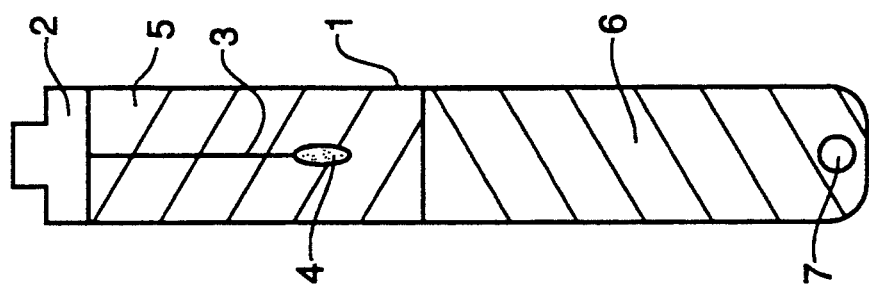

An electrode as shown generally in FIG. 1 of the accompanying drawings was made up, the electrode member being a silver wire coated with silver chloride.

The lower gelled solution (6) was prepared by dissolving 2 g of tris (hydroxymethyl)methyl acrylamide and 0.06 g N,N'-methylene-bis-acrylamide cross linking agent in 9.6 g of 3.5M potassium chloride solution with gentle heat and stirring. After cooling to ambient temperature polymerisation was initiated by the addition of 0.2 ml of 0.1M dipotassium disulphite dissolved in 3M potassium chloride solution. This was transferred to one end of a glass tube and allowed to set.

The upper solution was prepared by the addition of 2.5 g of tris(hydroxymethyl)methyl acrylamide to 7.5 g of 3.5M potassium chloride solution saturated with AgCl, with 0.3 ml of dipotassium disulphite solution (0.29 g in 10 ml of water). This produces a partly gelled viscous solution which can be transferred to the upper portion of the reference electrode.

The silver chloride-coated silver wire is then inserted into the upper electrolyte solution.

EXAMPLE 2

Figure 3:
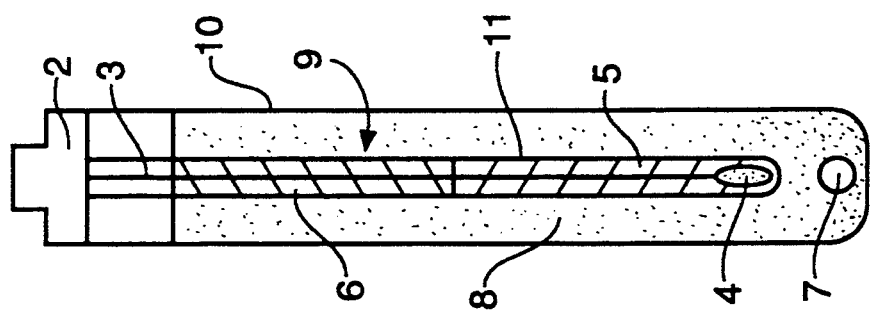
FIGS. 1, 2, 3 and 7 are schematic drawings of electrodes of the present invention.
Figure 2:
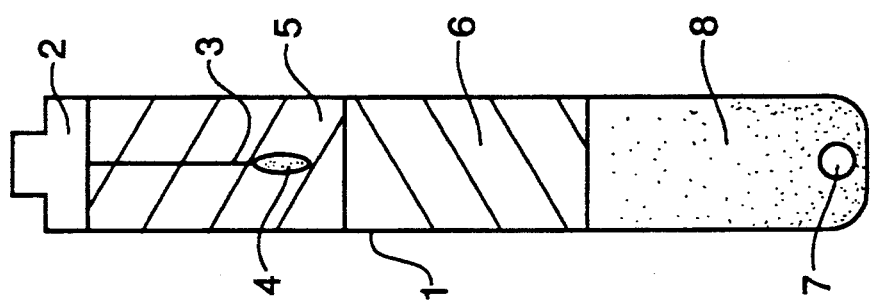

An electrode as shown generally in FIG. 2 of the accompanying drawings was made up in a similar way to that of Example 1. The potassium chloride gel, the upper viscous solution and electrode member were identical to that of Example 1.

The lower gel (8) was prepared by dissolving 2 g of tris(hydroxymethyl)methyl acrylamide and 0.06 g N,N'-methylene-bis-acrylamide cross linking agent in 10 ml of 2.6M mixed nitrate solution (2.21M potassium nitrate and 0.39M sodium nitrate).

After transferring to the electrode vessel, polymerisation was inititated at 40° C. by the addition of 0.2 ml each of 0.1M dipotassium peroxidisulphite (0.37 g in 10 ml water) and dipotassium disulphite (0.29 g in 10 ml of water).

Figure 4:
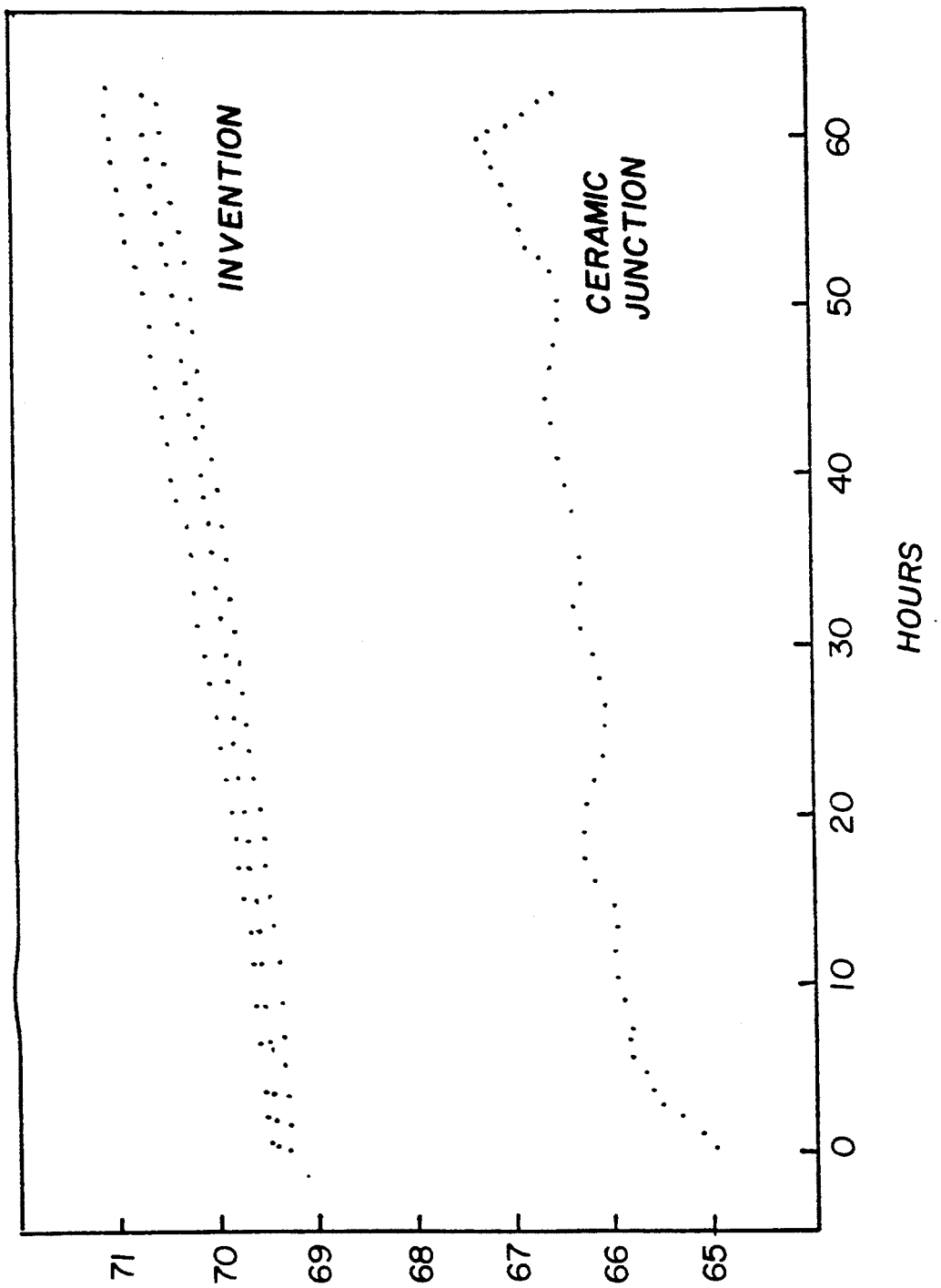
FIGS. 4, 5, and 6 show the results of the preferred embodiments plotted against that of ceramic junction and polyacrylamide reference electrodes.

Three samples of this electrode were tested for stability against a ceramic junction silver/silver chloride reference electrode by placing them in a test solution of 0.1M potassium nitrate and continuously recording the potential of each. The results are plotted in FIG. 4 which show that while there is a common slight drift upwards, the electrodes of the invention show straight line curves while the ceramic junction electrode shows considerable variations over the 60 hour period of the test.

Figure 5:
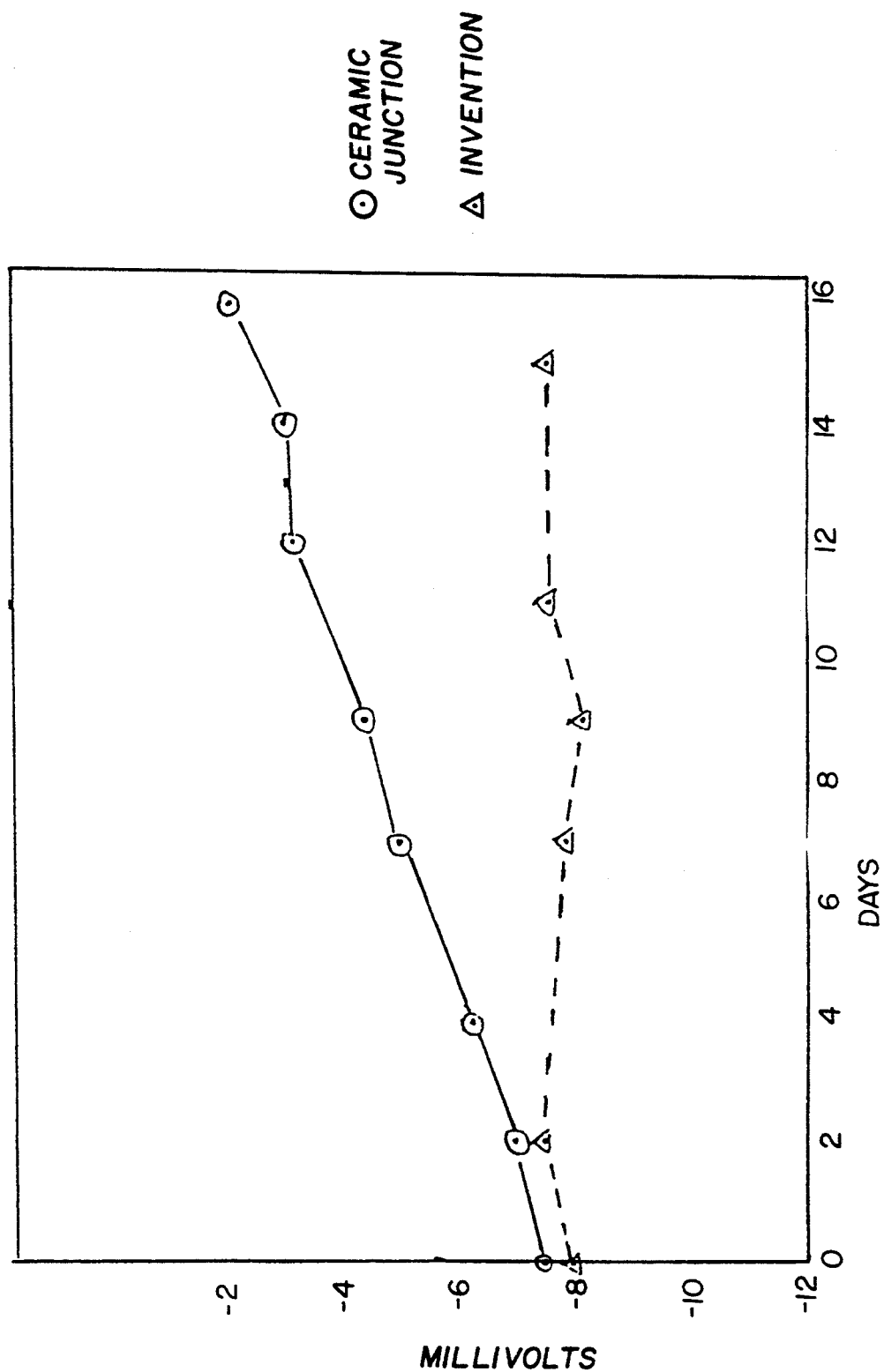

The electrode was placed in 0.1M potassium nitrate solution and tested against a ceramic junction electrode over a period of 16 days with readings being taken every 2 days. The results are plotted in FIG. 5. It can be seen that while the ceramic electrode displays an a continual upward drift, the electrode of the invention displays very little variation over the whole period.

Figure 6:
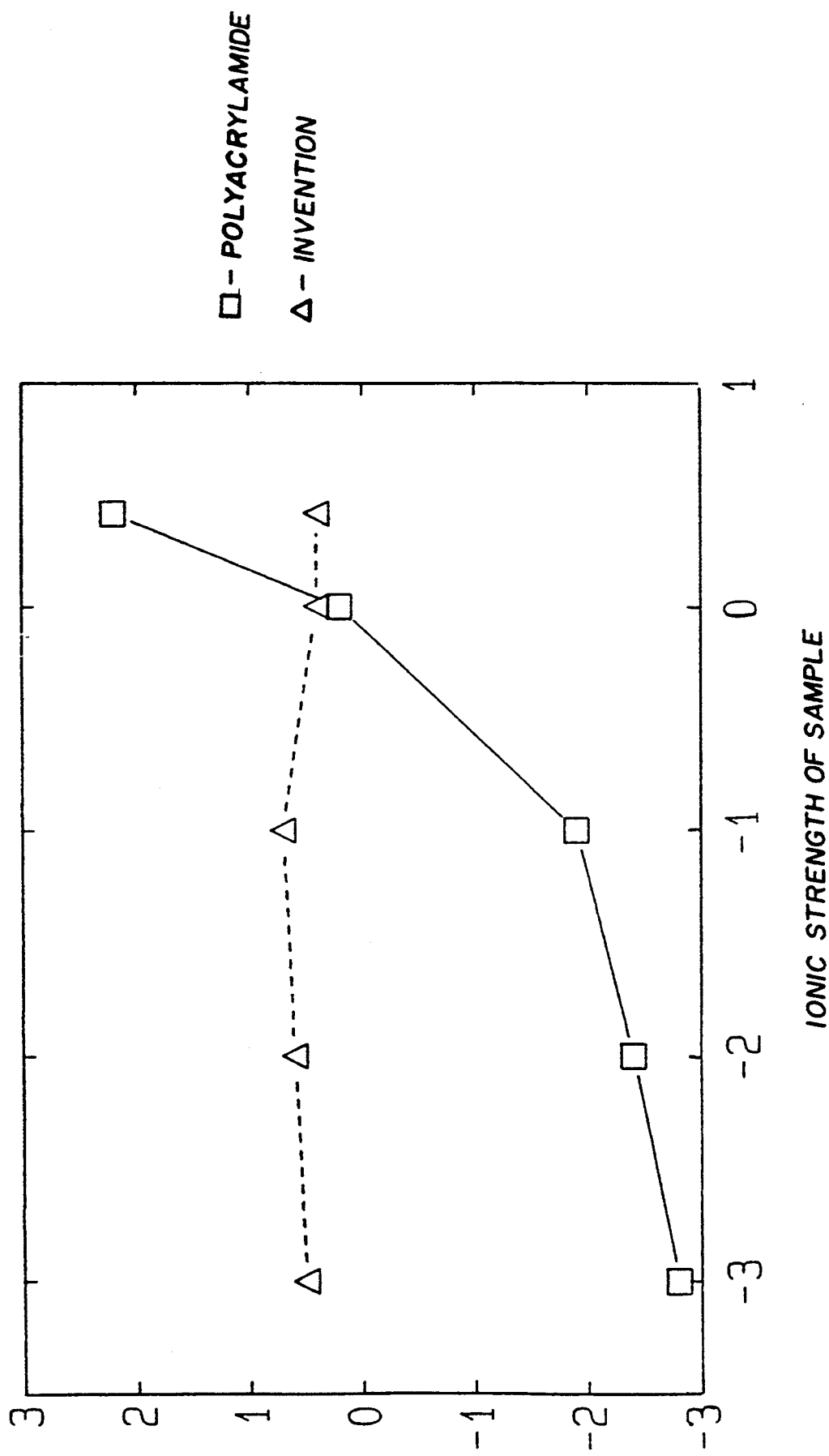

The electrode was also tested against a similar electrode in which the gelling agent was polyacrylamide (representing the prior art). The tests were conducted in a series of solutions of differing ionic strength against a free-flowing wick electrode. The results are plotted in FIG. 6 and show that the polyacrylamide gel electrode varies considerably while the electrode of the invention shows an essentially constant reading.

EXAMPLE 3

Figure 7:
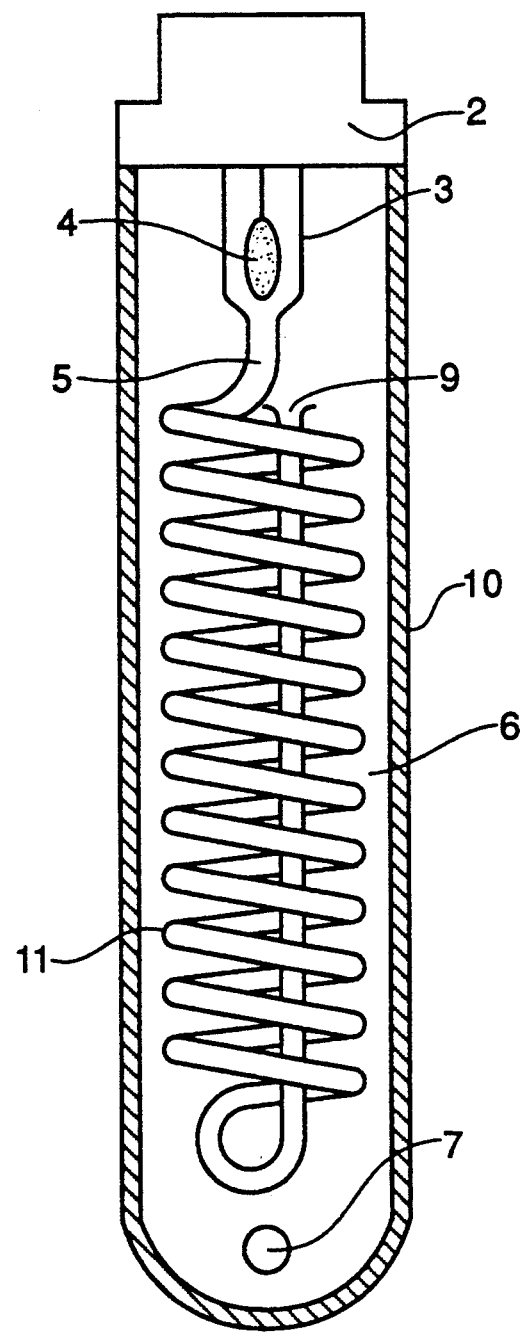

An electrode as shown generally in FIG. 7 was prepared.

The gel in the inner coiled vessel (11) was prepared by dissolving 3.5 g tris(hydroxymethyl)methyl acrylamide, 0.06 g N,N'-methylene-bis-acrylamide and 0.4 g triblock copoly(oxyethylene-oxypropylene-oxyethylene) (F-68) in 12 g of 2.8M potassium chloride solution saturated with silver chloride. The outer solution had the same composition as the inner solution except that the silver chloride was omitted.

We claim:

1. A half-cell reference electrode comprising an electrode member in electrochemical contact with a first gelled or viscous electrolyte solution which itself in electrochemical contact with a second gelled electrolyte solution wherein said second gelled electrolyte solution comprises a polymer containing acrylamide units substituted with a group or groups which lower the polymer's tendency to hydrolyse compared to polyacrylamide while providing a polymer that forms a gelled solution of a mixture of 2.21M Potassium Nitrate and 0.39M Sodium Nitrate, wherein a total molar concentration is a 2.6M sodium/potassium nitrate solution wherein the polymer and sodium potassium solution comprises at least 75% by weight sodium/potassium nitrate solution.

2. An electrode according to claim 1 wherein the polymer forms a gelled solution and said gelled 2.6M sodium/potassium nitrate solution comprises from 75% to 90% by weight sodium/potassium nitrate solution.

3. An electrode according to claim 1 or 2 wherein a first gelled electrolyte solution is itself in contact with a second gelled electrolyte solution which is contactable with the liquid to be tested or wherein the first gelled electrolyte is replaced by a viscous electrolyte solution which is in contact with the second gelled electrolyte solution.

4. An electrode according to claim 1 wherein the second gelled electrolyte solution is itself in electrochemical contact with a third gelled electrolyte solution.

5. An electrode as claimed in claim 1 in which the polymer comprising units derived from tris(hydroxymethyl)methyl acrylamide.

6. An electrode as claimed in claim 5 in which the tris(hydroxymethyl)methyl acrylamide units are cross-linked.

7. An electrode as claimed in claim 6 in which the tris(hydroxymethyl)methyl acrylamide units are cross-linked with N,N'-methylene-bis-acrylamide, tetraethylene glycol dimethacrylate, 1,4-butanediol dimethacrylate, ethylene diacrylate or ethylene glycol dimethacrylate.

8. An electrode as claimed in claim 1 in which the electrode member is a calomel reference element, a redox reference element, a silver wire at least partially coated with silver chloride, or a silver/silver chloride cartridge reference element.

9. An electrode as claimed in claim 1 in which the first gelled electrolyte or viscous electrolyte comprises a potassium chloride/silver chloride solution.

10. An electrode as claimed in claim 1 wherein the second gelled electrolyte comprises a potassium chloride solution.

11. An electrode as claimed in claim 4 in which the third gelled electrolyte comprises a mixed sodium/potassium nitrate solution.

12. An electrode as claimed in claim 1 in which one or more of the gelled electrolyte solutions further contain glycerol, ethylene glycol, polyethylene glycol, polyvinyl alcohol, silica gel or a polyoxyethylene-polyoxypropylene-polyoxyethylene triblock copolymer as a water evaporation inhibitor.

13. The electrode of claim 1 wherein said first electrolyte solution comprises a viscous electrolyte solution.

14. The electrode of claim 1 wherein said first electrolyte solution a gelled electrolyte solution.

15. The electrode of claim 1 further comprising a vessel encasing said electrode and wherein said vessel is provided with an aperture for electrochemical contact of said electrode and any solution the vessel contacts.

16. The electrode of claim 1 wherein said gelled 2.6M sodium/potassium nitrate solution comprises 80 to 90 percent by weight sodium/potassium nitrate solution.

17. A half-cell reference electrode comprising an electrode member in electrochemical contact with at least one gelled electrolyte solution comprising a polymer containing acrylamide units substituted with a group or groups which lower the polymer'tendency to hydrolyse compared to polyacrylamide while providing a polymer that forms a gelled solution of a mixture of 2.21M Potassium Nitrate and 0.39M Sodium Nitrate, wherein a total molar concentration is a 2.6M sodium/potassium nitrate solution wherein the polymer and gelled sodium/potassium nitrate solution comprises at least 75% by weight sodium/potassium nitrate solution.

18. An electrode according to claim 17 wherein a viscous electrolyte solution is in contact with said at least one gelled electrolyte solution said viscous electrolyte comprises a polymer containing acrylamide units substituted with a group or groups which lower the polymer'tendency to hydolyse compared to polyacrylamide while providing a polymer that forms a gelled solution in 2.6M sodium/potassium nitrate solution wherein the gelled polymer and sodium/potassium nitrate solution comprises at least 75% by weight sodium/potassium nitrate solution.

19. An electrode according to claim 17 wherein the polymer forms a gelled solution and said gelled 2.6M sodium/potassium nitrate solution comprises from 75% to 90% by weight sodium/potassium nitrate solution.

20. An electrode according to claim 18 wherein the said at least one gelled electrolyte solution is itself in electrochemical contact with a third gelled electrolyte solution.

21. An electrode as claimed in claim 17 in which the polymer comprises units derived from tris(hydroxymethyl)methyl acrylamide.

22. An electrode as claimed in claim 21 in which the tris(hydroxymethyl)methyl acrylamide units are cross-linked.

23. An electrode as claimed in claim 22 in which the tris(hydroxymethyl)methyl acrylamide units are cross-linked with N,N'-methylene-bis-acrylamide, tetraethylene glycol dimethacrylate, 1,4-butanediol dimethacrylate, ethylene diacrylate or ethylene glycol dimethacrylate.

24. An electrode as claimed in claim 17 in which the electrode member is a calomel reference element, a redox reference element, a silver wire at least partially coated with silver chloride or a silver/silver chloride cartridge reference element.

25. An electrode as claimed in claim 18 wherein the second gelled electrolyte comprises a potassium chloride solution.

26. An electrode as claimed in claim 20 in which the third gelled electrolyte comprises a mixed sodium/potassium nitrate solution.

27. An electrode as claimed in claim 17 in which one or more of the gelled electrolyte solutions further contain glycerol, ethylene glycol, polyethylene glycol, polyvinyl alcohol, silica gel or a polyoxyethylene-polyoxypropylene-polyoxyethylene triblock copolymer as a water evaporation inhibitor.

28. The electrode of claim 17 further comprising a vessel encasing said electrode and wherein said vessel is provided with an aperture for electrochemical contact of said electrode and any solution the vessel contacts.

29. The electrode of claim 17 wherein said gelled 2.6M sodium/potassium nitrate solution comprises 80 to 90 percent by weight sodium/potassium nitrate.

* * * * *

UNITED STATES PATENT AND TRADEMARK OFFICE
CERTIFICATE OF CORRECTION

PATENT NO. : 5,360,529
DATED : Nov. 1, 1994
INVENTOR(S) : Stephen J. Edwards et al.

It is certified that error appears in the above-indentified patent and that said Letters Patent is hereby corrected as shown below:

Column 6, line 8, after first occurrence of "solution" insert --comprises--.

Column 6, line 21, "polymer'tendency" should read --polymer's tendency--.

Column 6, line 34, "polymer'tendency" should read --polymer's tendency--.

Signed and Sealed this

Thirtieth Day of January, 1996

*Attest:*

BRUCE LEHMAN

*Attesting Officer*  *Commissioner of Patents and Trademarks*